United States Patent
Liversidge

(10) Patent No.: US 10,213,561 B2
(45) Date of Patent: Feb. 26, 2019

(54) MEDICAL NEEDLE COVER ARRANGEMENT

(75) Inventor: Barry Peter Liversidge, Colchester (GB)

(73) Assignee: TIP-TOP.COM LTD (GB)

( * ) Notice: Subject to any disclaimer, the term of this patent is extended or adjusted under 35 U.S.C. 154(b) by 1037 days.

(21) Appl. No.: 13/577,771

(22) PCT Filed: Feb. 11, 2011

(86) PCT No.: PCT/GB2011/050266
§ 371 (c)(1),
(2), (4) Date: Sep. 4, 2012

(87) PCT Pub. No.: WO2011/098831
PCT Pub. Date: Aug. 18, 2011

(65) Prior Publication Data
US 2012/0330243 A1    Dec. 27, 2012

(30) Foreign Application Priority Data
Feb. 11, 2010   (GB) .................................. 1002327.3

(51) Int. Cl.
*A61M 5/32* (2006.01)
*A61M 5/31* (2006.01)

(52) U.S. Cl.
CPC ... *A61M 5/3213* (2013.01); *A61M 2005/3109* (2013.01)

(58) Field of Classification Search
CPC .............. A61M 5/3202; A61M 5/3213; A61M 2005/3109; A61M 2005/3247; A61M 5/3204; A61M 5/3215
See application file for complete search history.

(56) References Cited

U.S. PATENT DOCUMENTS 4,964,866 A * 10/1990 Szwarc ............... A61M 5/3202
                                                                  604/192
5,697,908 A * 12/1997 Imbert ............... A61M 5/3243
                                                                  604/110
(Continued)

FOREIGN PATENT DOCUMENTS

EP   1502617       2/2005
EP   1932558 A1    6/2008
(Continued)

OTHER PUBLICATIONS

International Search Report, PCT International Application No. PCT/US2011/050266, dated May 25, 2011.
(Continued)

*Primary Examiner* — Emily L Schmidt
(74) *Attorney, Agent, or Firm* — Grossman Tucker Perreault & Pfleger PLLC

(57) ABSTRACT

A medical needle cover arrangement for a single-use syringe having a medical needle with a sharp tip, the needle being mounted on the syringe to project forwardly from a needle hub. A sleeve forming a part of a safety device is mounted on the syringe. The sleeve is arranged for axial movement with respect to the needle from an initial shielding position to a non-shielding position, the sleeve being blocked against forward movement with respect to the syringe from its initial shielding position. A soft needle cover overlies the needle with the sharp tip of the needle sealed by the cover. The rear end of the soft needle cover and the forward end of the syringe hub are profiled with complementary engaging surfaces. The cover has a step part-way between its ends, the step being engaged by an internal abutment at the forward end of the sleeve, to resist movement of the cover forwardly away from the syringe hub and so maintain a seal between the cover and hub. The part of the cover between the hub and (Continued)

the step may be subjected to compression to enhance the sealing effect.

9 Claims, 8 Drawing Sheets

(56) References Cited

U.S. PATENT DOCUMENTS

| | | | |
|---|---|---|---|
| 5,741,236 A * | 4/1998 | Kakiuti | A61M 5/001 604/192 |
| 5,858,008 A | 1/1999 | Capaccio | |
| 6,514,229 B1 | 2/2003 | Huang et al. | |

FOREIGN PATENT DOCUMENTS

| | | | |
|---|---|---|---|
| EP | 1964586 | 9/2008 | |
| WO | 2009016428 | 2/2009 | |
| WO | WO 2009155277 A1 * | 12/2009 | A61M 5/2033 |

OTHER PUBLICATIONS

EP Examination Report dated Mar. 2, 2015, received in related EP Application No. 11706917.9, 4 pgs.
National Institute for Occupational Safety and Health, Preventing Needlestick Injuries in Health Care Settings,U.S. Department of Health and Human Services, Nov. 1999, 28 pages.

* cited by examiner

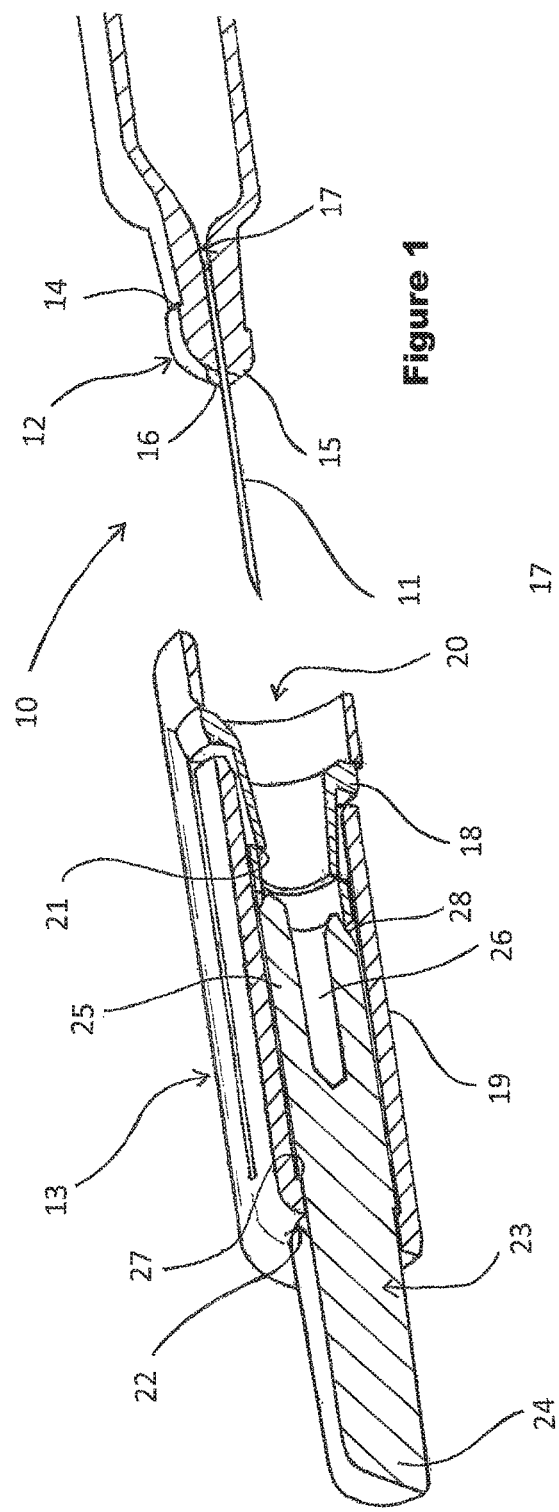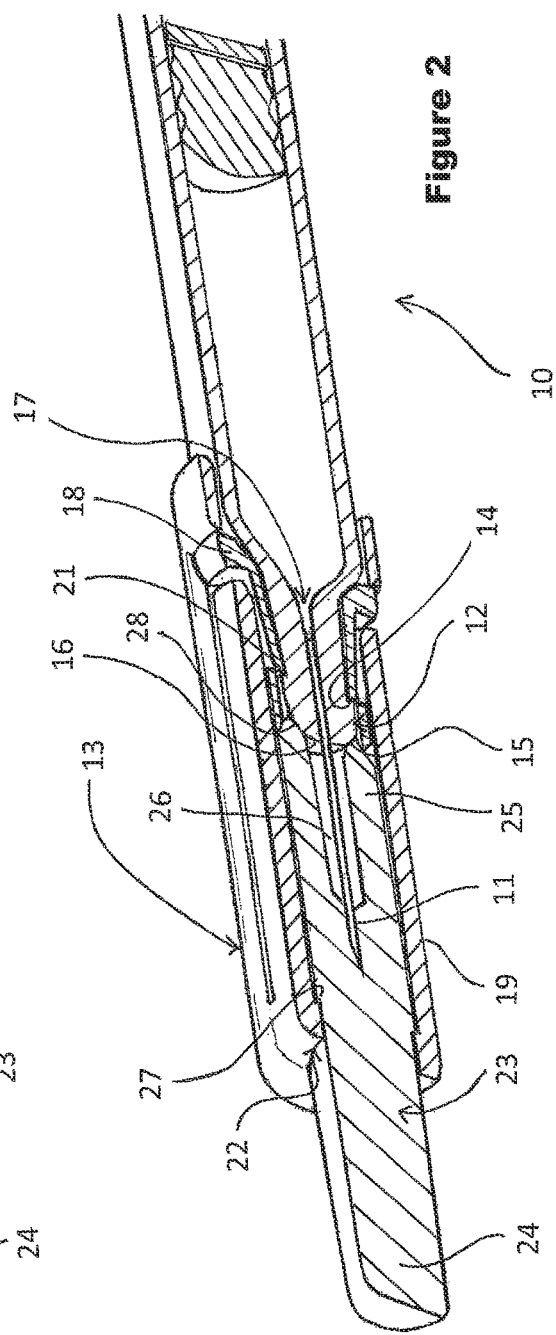

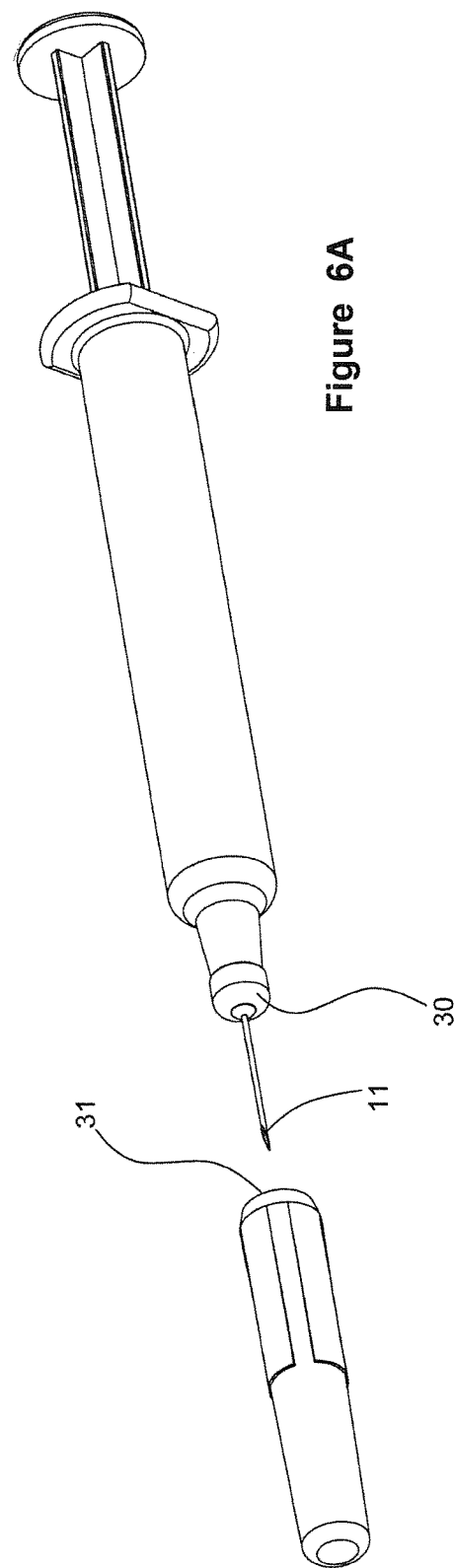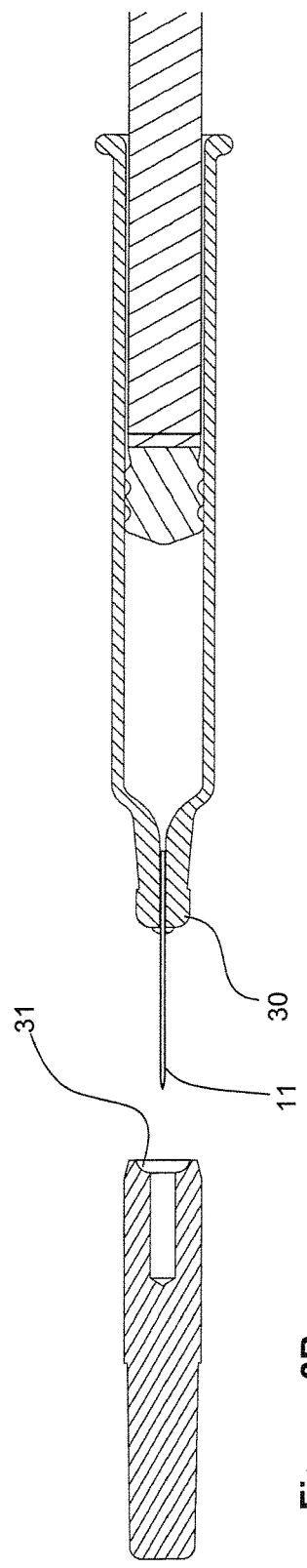
Figure 6A
Figure 6B

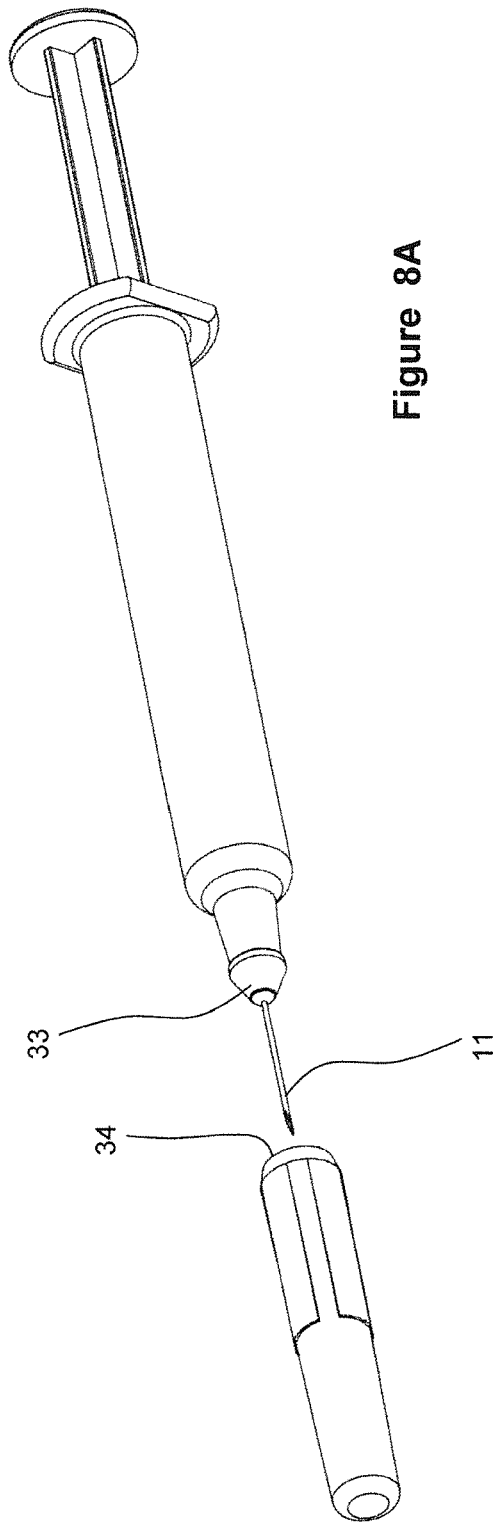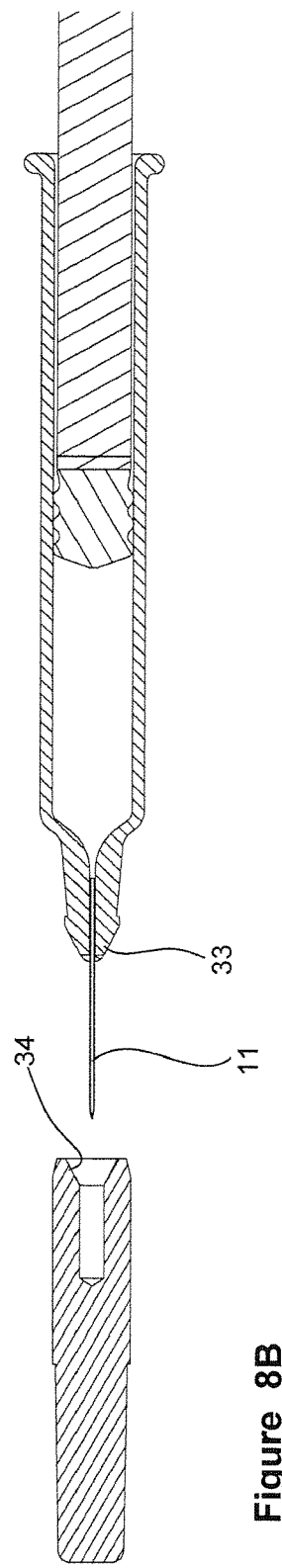
Figure 8A
Figure 8B

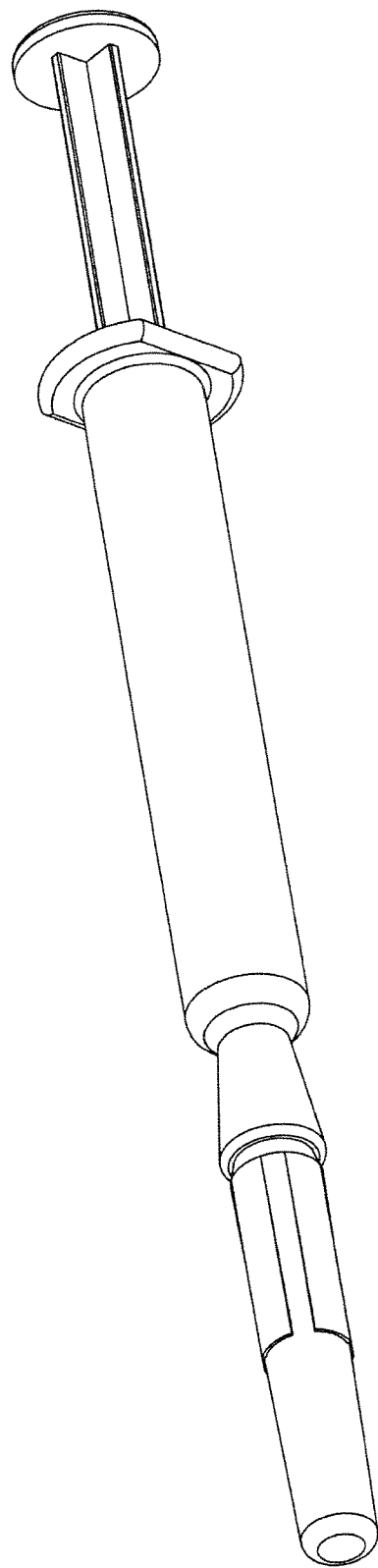
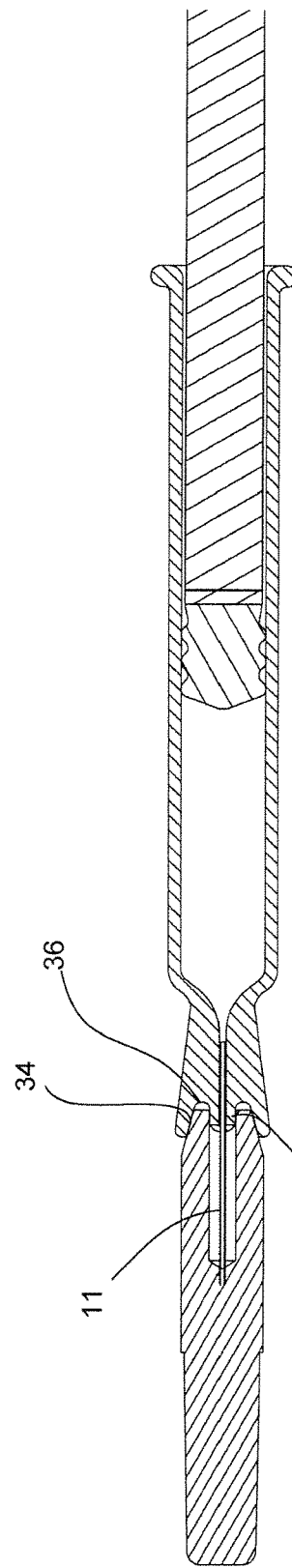
Figure 11A
Figure 11B

MEDICAL NEEDLE COVER ARRANGEMENT

CROSS REFERENCE TO RELATED APPLICATION

The present application is the U.S. national stage application of International Application PCT/GB2011/050266, filed Feb. 11, 2011, which international application was published on Aug. 18, 2011 as International Publication WO 2011/098831 A1. The International Application claims priority of British Patent Application 1002327.3, filed Feb. 11, 2010.

This invention relates to a medical needle cover arrangement for a soft needle cover used in association with a syringe having a medical needle projecting forwardly therefrom. In its preferred aspects, this invention concerns improvements in a soft needle cover associated with a needle safety device arranged to confer passive protection to a medical needle projecting forwardly from a single-use syringe.

A syringe provided with a medical needle as employed in this invention is intended to be used to penetrate a human or animal body, or for other medical uses such as the penetration of a pierceable membrane of an intravenous medication system. In the following all medical uses of the syringe and needle will be described simply as the penetration of a body, even though specific embodiments may be intended for other medical uses.

Throughout this specification the terms "forward" and "forwardly" used in relation to the syringe, needle and needle safety device refer to those ends of the components which are approached to a body when a procedure is to be performed, and the direction towards those ends. Conversely, the terms "rearward" and "rearwardly" refer to those ends of the components opposed to the forward ends and the direction away from those forward ends.

A syringe having a needle permanently secured thereto is frequently pre-filled with a liquid drug or medicament and then is used only once to perform an injection. Once used, the syringe and needle must be disposed of in a safe manner. To protect any people who might have to handle such a syringe, either before or after performing an injection, it is becoming a requirement of health and safety legislation as well as best practice to provide the needle with some kind of safety device to minimise the risk of accidental needle-stick injury. Such a safety device preferably operates on a "passive" basis—that is to say, without the need for a user to undertake any action to ensure the needle is protected.

Typically, such a safety device may have a sleeve which is mounted on the syringe and is slidable axially between a needle protecting position and a non-protecting position. A spring may bias the sleeve forwardly relative to the syringe to the protecting position, the sleeve being moved rearwardly relative to the syringe in the course of performing an injection whereafter the sleeve moves forwardly back to its protecting position under the force of the spring at the completion of the injection. The safety device may be provided with a locking arrangement to prevent the sleeve moving rearwardly from its protecting position for a second time, after the performance of an injection.

In the course of manufacture of a single-use syringe having a needle permanently secured to a needle hub at the forward end of the syringe barrel, it is the usual practice to fit a needle cover over the needle before the syringe is sterilised and then packaged for storage and transport, prior to filling with a liquid drug or other medicament. Such a cover is usually made of a soft elastomer such as a TPE and must be compliant with drug compatibility and stability. The rear end of the cover fits on to the needle hub and the sharp tip of the needle penetrates the material of the cover so as to be sealed thereby, but the cover does not bear on the greater part of the length of the needle so as not to remove any lubricant which is usually be applied to the needle. Thus, there is a void around the greater part of the needle, from the hub of the syringe to a location adjacent the sharp tip of the needle.

A significant problem associated with the manufacturing process for a single-use syringe is that in the course of the sterilisation and packaging steps, there is a tendency for a needle cover to be displaced from its as-fitted condition on the hub—a phenomenon known as "pop-off". This primarily occurs on account of the changes of pressure to which the syringe and cover are subjected in the course of the cleaning and sterilising steps and the fact that the void between the needle and the cover is in effect a sealed space. The problem has been addressed by venting that space, but then there is a possibility that the sterile condition of the needle may be compromised. As a consequence, in an attempt to increase the security of the attachment of a needle cover to the hub of a syringe, it is the usual practice to provide at least one formation on the hub of the syringe and a corresponding formation at the rear end of the needle cover to co-operate with the formation on the hub, mechanically to hold the cover on the hub. For example, an upstanding rib may be formed around the hub, the needle cover having an in-turned flange at its rear end and which is fitted over the rib to engage therebehind and so hold the cover on to the syringe hub.

When a syringe and cover as described above is to be fitted with a needle safety device, it is highly advantageous for the needle safety device to have the smallest possible external dimensions and so the interior of the device must fit closely to the syringe. This can lead to a problem associated with the removal of the cover. When the cover is to be pulled off the needle, the rear end of the cover must expand sufficiently for the flange thereof to slide over the rib on the hub of the syringe, but there may be insufficient room within the needle safety device to permit this expansion of the rear end of the cover.

It is a principal aim of the present invention to minimise the problems discussed above of providing a soft needle cover on a single-use syringe having a needle secured to the forward end thereof and in particular to minimise the phenomenon of "pop-off" associated with the manufacture of conventional pre-filled single-use syringes.

According to one aspect of this invention, a medical needle cover arrangement comprises a syringe, a medical needle having a sharp tip mounted on the syringe to project forwardly therefrom, a needle shield mounted on the syringe for rearward axial movement with respect to the needle from an initial shielding position to a non-shielding position, and a soft needle cover overlying the needle, the rear end of the soft needle cover and the forward end of the syringe being profiled with complementary engaging surfaces, wherein the shield is blocked against forward movement with respect to the syringe from the initial shielding position and is adapted to engage the cover forwardly of the rear end thereof to resist movement of the cover forwardly away from the syringe.

It will be appreciated that in this invention, a seal is formed between the rear end of the soft needle cover and the forward end of the syringe by virtue of correspondingly-profiled engaging surfaces on the syringe and cover. So long as a safety device including a shield for the needle is fitted to the syringe to provide the engagement between the cover and the shield, there is no need for the cover to be held on to the syringe hub by mechanical interengagement of formations on the syringe hub and the cover, such as an in-turned flange which engages behind a rib formed around the hub of the syringe. In this invention, the seal is formed forwardly of any rib or other formation provided on the hub of the syringe. The engagement between the cover and the shield when in the shielding position serves to prevent the cover sliding off the hub of the syringe during the manufacturing process or subsequently, by virtue of the fact that the shield is blocked against forward movement from the shielding position. As such, the integrity of the seal between the cover and the hub of the syringe may be maintained, even during the sterilisation process which usually subjects the closed space around the needle to differential pressure.

As with a conventional soft needle cover, the sharp tip of the needle may be received in the material of the cover so as to be sealed thereby. In addition, this confers further protection to the sharp tip of the needle in the various stages of the manufacture of the syringe, its sterilisation, packaging, subsequent unpacking for filling, filling and re-packaging.

The engagement of the shield and cover may introduce a compressive force in the cover, between the rear end of the cover and the location where the sleeve engages the cover. This urges the rear end of the cover rearwardly, to ensure a seal is maintained between the cover rear end and the syringe hub. In view of the resilient nature of the cover, the compression of the cover will be maintained during manufacture, transport and storage of the syringe, so in turn ensuring that an effective seal is also maintained.

This invention is not restricted to any particular kind of safety device for use with the syringe, so long as the safety device is connectable (or has been connected) directly or indirectly to the syringe and engages the soft cover for the needle, to hold the rear end of the cover to the syringe hub. Preferably, the shield is in the form of a sleeve mounted directly or indirectly on the syringe for sliding movement over the syringe barrel, between the shielding position and a non-shielding position spaced axially rearwardly (with respect to the syringe) of the shielding position. A spring may urge the sleeve forwardly with respect to the barrel to the shielding position such that the needle will be protected after use. The cover may serve to prevent the sleeve sliding rearwardly until the cover has been stripped away from the device, preparing the syringe for use. A single piece sleeve may be employed or the sleeve may comprise two or more sleeves which may telescope, especially in the case of a relatively long needle.

According to various other aspects of this invention, there is provided an assembly of a single-use syringe having a hub at the forward end thereof, a medical needle projecting forwardly from the syringe hub, a soft needle cover overlying the needle and having a rear end in engagement with the syringe hub, a shield mounted on the syringe for rearward axial movement with respect to the needle from an initial shielding position to a non-shielding position, the shield being blocked against forward movement with respect to the syringe from the initial shielding position and being adapted to engage the cover forwardly of the rear end thereof to resist movement of the cover forwardly away from the syringe, wherein a seal is formed between the cover rear end and the syringe hub, and one or more of:

(a) the forward movement of the cover is resisted solely by the engagement of the cover with the sleeve;
(b) the seal is formed without mechanical interlocking of the cover rear end and the hub;
(c) the seal is formed between substantially radial, conical or arcuate interengaging surfaces of the cover rear end and hub.

This invention extends to a method of effecting a seal between a soft needle cover and a needle hub forming a part of a single-use syringe and from which a needle projects forwardly, there being a needle shield mounted on the syringe for rearward axial movement with respect to the needle from an initial shielding position to a non-shielding position, and the rear end of the needle cover having a complementary profile to that at the forward end of the needle hub, in which method the shield is blocked against forward movement from its initial shielding position and a part of the shield engages the cover at a location spaced forwardly from the rear end thereof, whereby the portion of the cover between said location and the rear end of the cover is subjected to a compressive force, thereby effecting and maintaining a seal between the rear end of the cover and the needle hub.

By way of example only, certain specific embodiments of soft cover sealing arrangements of this invention will now be described in detail, reference being made to the accompanying drawings in which:—

FIGS. 1 and 2 show a first embodiment of syringe and co-operating soft needle cover, FIG. 1 being a cut away isometric drawing showing a safety device carrying the soft needle cover before assembly to a syringe, and FIG. 2 showing the safety device fitted to the syringe;

FIGS. 6A, 6B, 7A and 7B are respectively axial sections and isometric views showing alternative interengaging faces between a soft needle cover and the hub (or nose) of a syringe;

Figure 3:
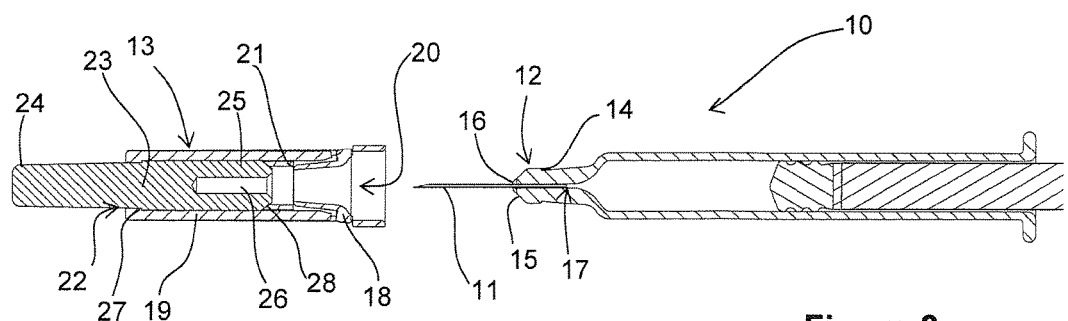
FIGS. 3 to 5 are axial section views through the first embodiment, with FIG. 3 corresponding to FIG. 1, FIG. 4 to FIG. 2 and FIG. 5 showing the cover stripped away from the safety device.

FIGS. 8A, 8B, 9A and 9B correspond to FIGS. 6A, 6B, 7A and 7B but show another possibility for interengaging faces between a soft needle cover and the hub of a syringe; and FIGS. 10A, 10B, 11A and 11B correspond to FIGS. 6A, 6B, 7A and 7B but show yet another possibility for interengaging faces between a soft cover and the hub of a syringe.

Referring initially to FIGS. 1 to 5, there is shown a syringe 10 having a needle 11 staked-in to the nose 12 of the syringe, and a safety device 13 to confer protection on the needle. The precise details of the safety device and its operation, particularly as concerns the possible locking of the safety device sleeve after performing an injection, form no part of this invention and will not be described in detail here. It is to be understood that this invention is not limited to the use of any particular safety device.

The nose of the syringe serves as a hub for the needle and defines a rearwardly facing shoulder 14 and forwardly of that shoulder the nose is given a generally conical profile which defines an engagement face 15. Centrally of the nose, a small mass of adhesive 16 serves to lock the needle 11 in a bore 17 extending through the nose 12. The safety device 13 includes a carrier 18 for a protective sleeve 19, slidable rearwardly with respect to the needle 11, when an injection is to be performed. The carrier has a bore 20 for the nose of the syringe, an inwardly directed rib 21 being formed in the bore for engagement behind the shoulder 14 when the safety device is fitted to the syringe 10 so as to hold that safety device to the syringe.

The protective sleeve 19 has at its forward end a circular opening 22 within which is located a soft rubber cover 23, the cover having a forward portion 24 extending beyond the sleeve and a rearward portion 25 disposed within the sleeve. A bore 26 extends into the cover from the rearward end thereof, for a distance less than the exposed length of the needle 11 projecting from the nose 12 of the syringe 10. The external surface of the cover has a step 27 partway between its ends, which engages the internal surface of the sleeve at the forward end, to retain the cover within the sleeve unless the forward portion 24 is pulled with a sufficient force to release the cover from the sleeve.

Figure 4:
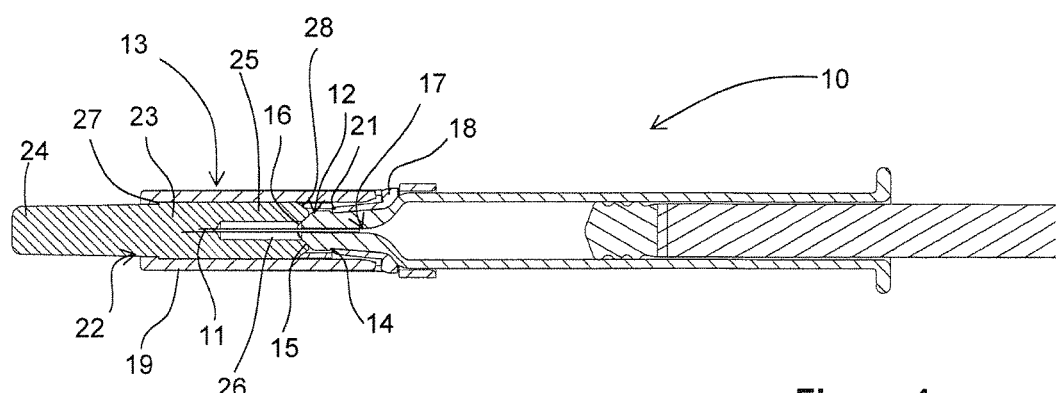

The rearward end face 28 of the cover around the bore 20 has a profile complementary to that of the conical engagement face 15 of the nose of the sleeve. The length of the cover, from that end face to the step 27 is such that on fitting the safety device to the syringe, as shown in FIGS. 2 and 4, the cover end face 28 engages with the syringe nose engagement face 15 and is resiliently urged into engagement therewith by pushing the safety device fully home on the nose of the syringe. Thus, the rearward portion 25 of the cover is subjected to axial compression by the fitting of the safety device to the syringe, ensuring a substantially airtight seal between the cover and the nose of the syringe, as shown in FIGS. 2 and 4.

As shown, the sharp tip of the needle is sealed by penetrating to a small extent the soft rubber cover. This serves to prevent the possibility of drug leakage from the needle but by having only the tip of the needle in the cover, lubricant provided on the needle to assist easy penetration of a body will not be wiped away by the cover. Further, the interengagement of the cover end face 28 with the syringe nose engagement face 15 effects a seal which ensures the needle remains sterile, so long as the assembly of the components has been undertaken in sterile conditions.

Figure 5:
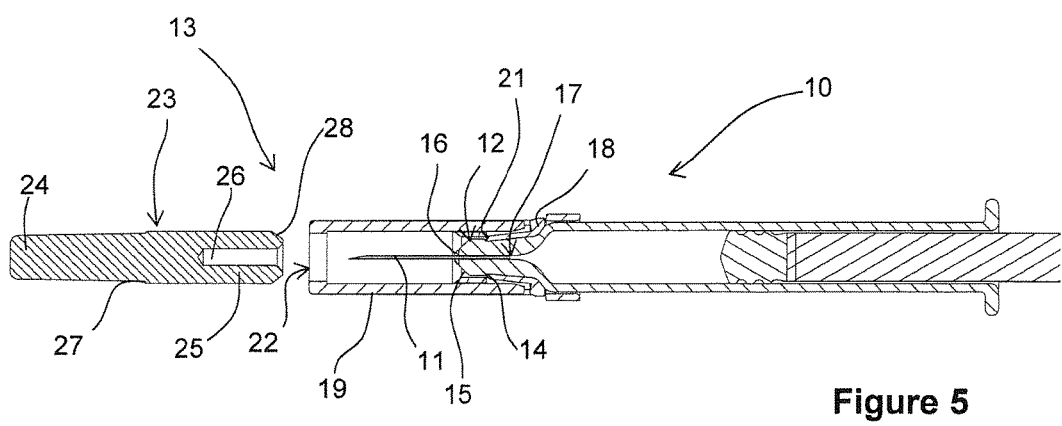
Figure 7A:
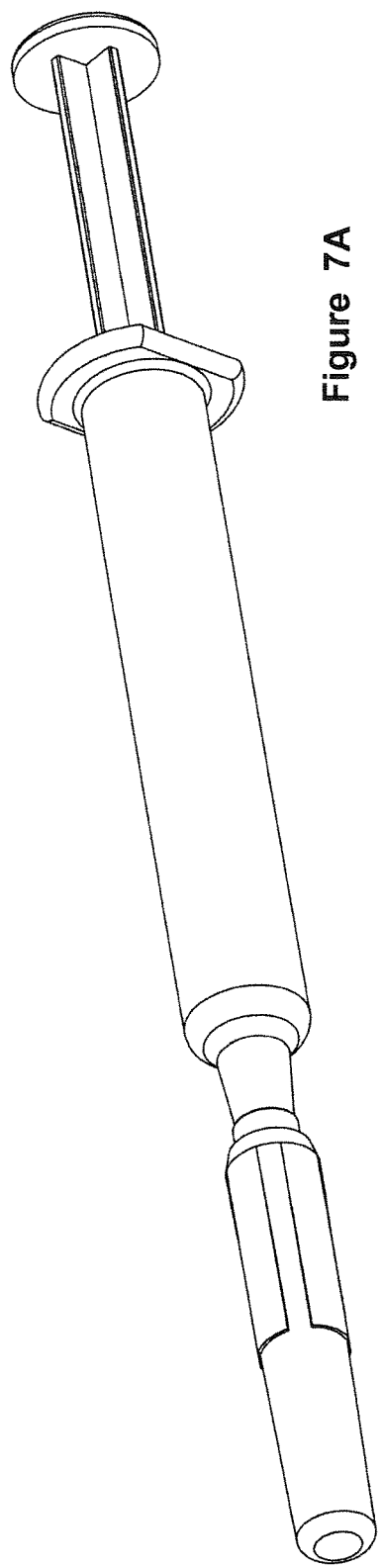
Figure 7B:
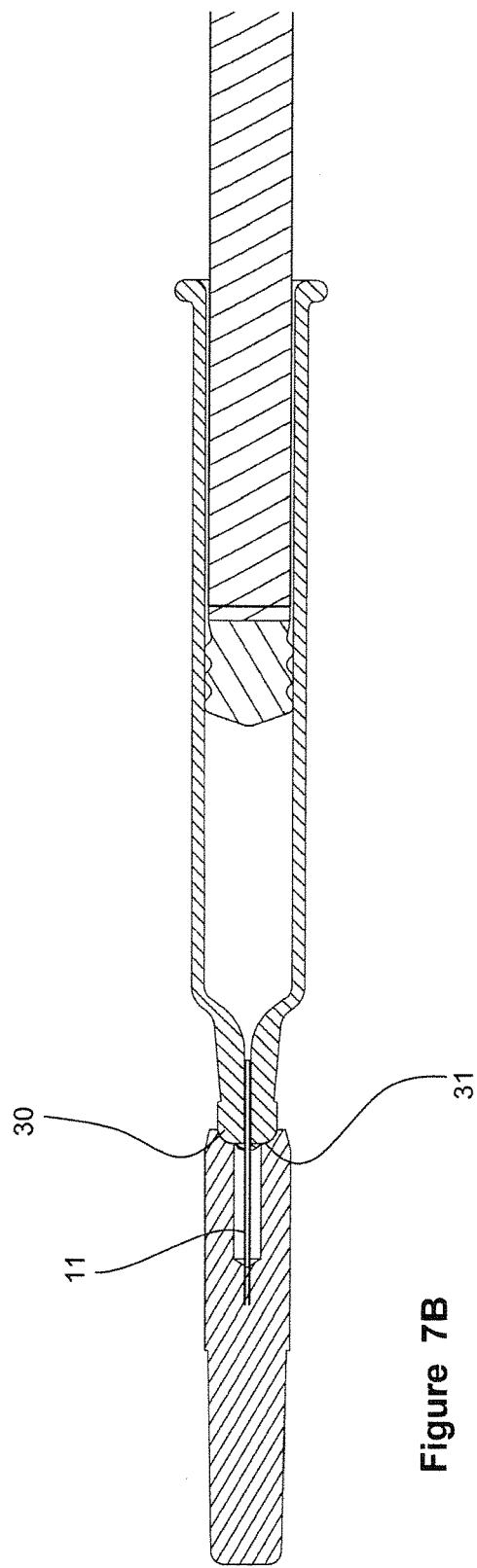
Figure 9A:
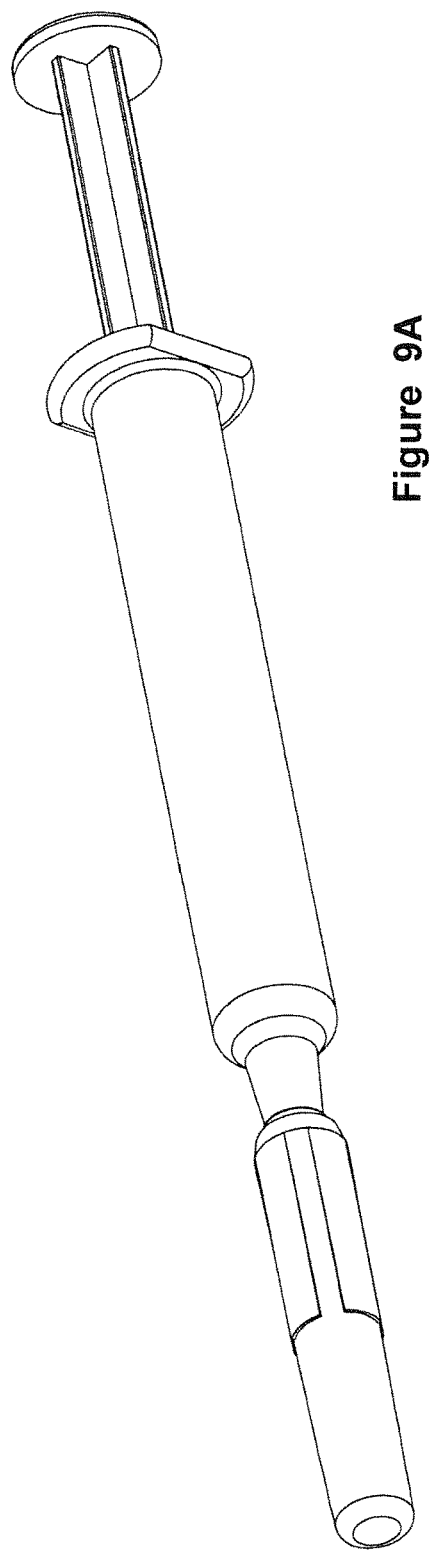
Figure 9B:
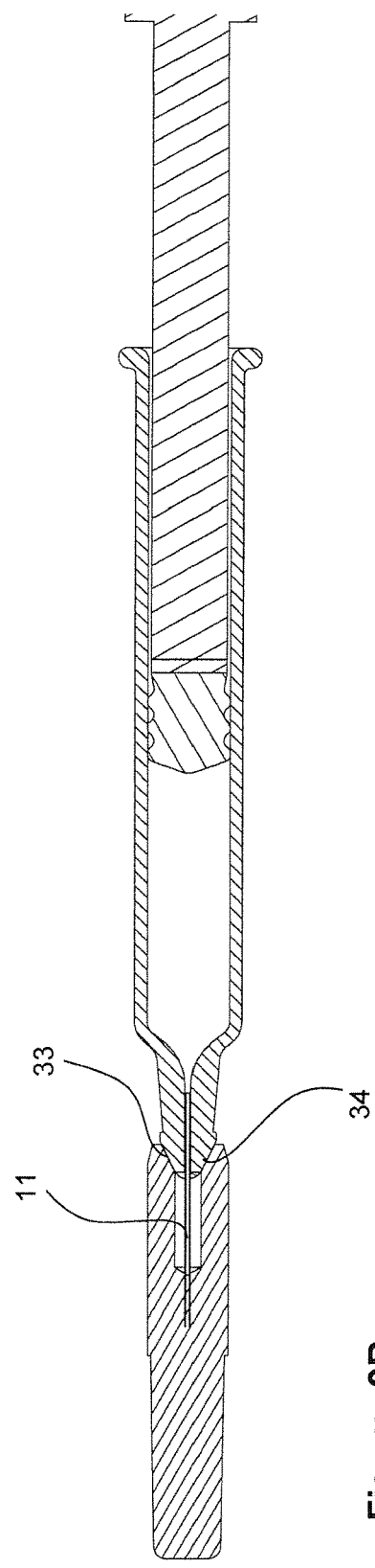
Figure 10A:
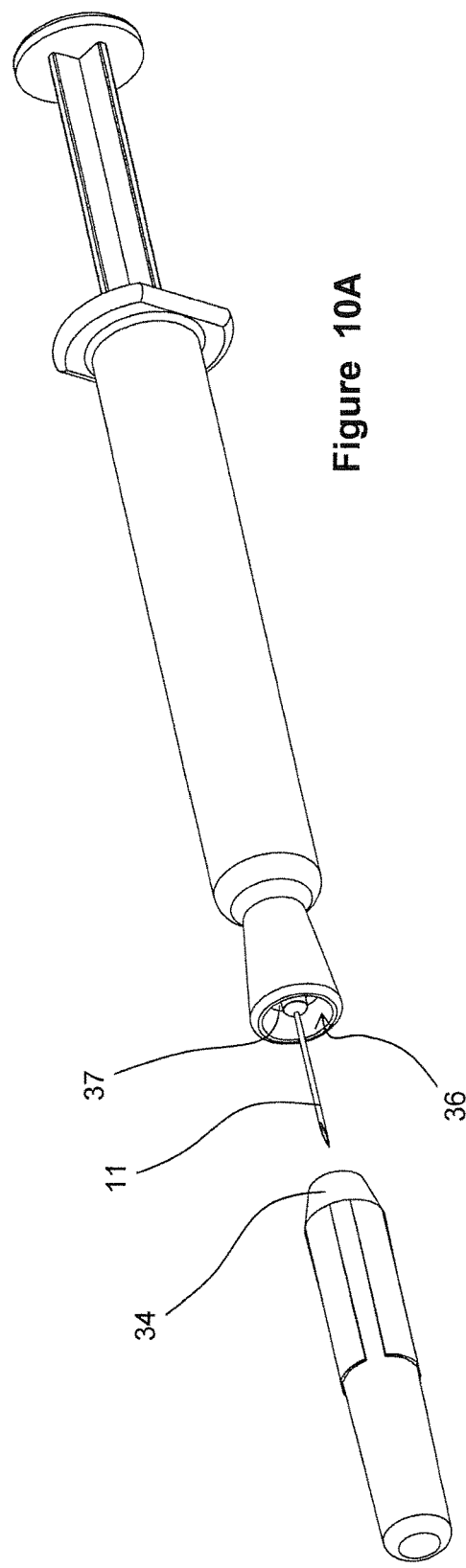
Figure 10B:
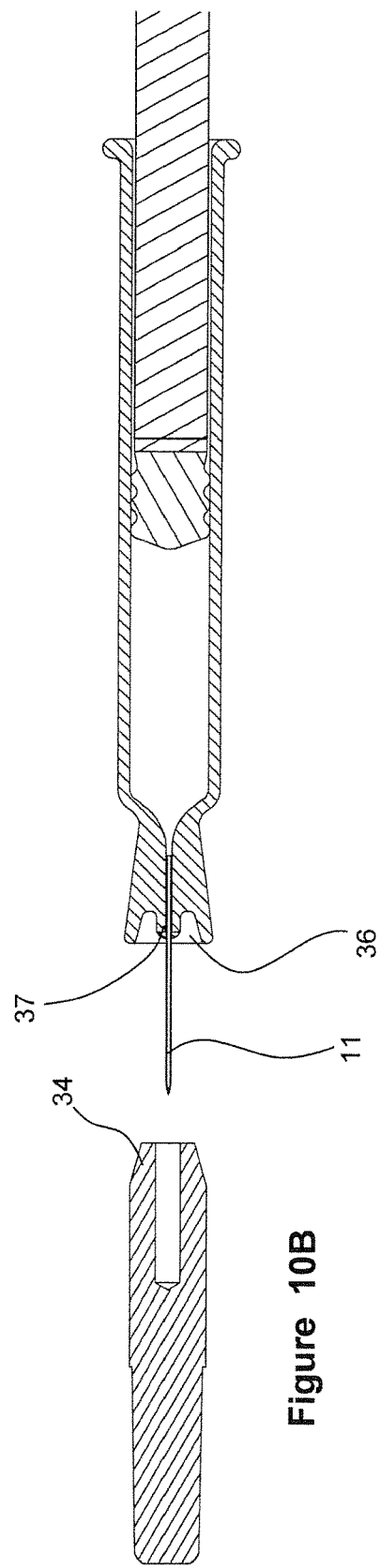

When the syringe and safety device are to be used, the forward portion 24 of the cover 23 is grasped and pulled away from the safety device 13 and syringe 10 (FIG. 5). The cover compresses radially to a sufficient extent to allow the step 27 to pass through the circular opening 22 at the forward end of the sleeve and then may be discarded, with the syringe and safety device ready for performing an injection.

FIGS. 6A, 6B, 7A and 7B show a second embodiment generally similar to that described above but in these drawings, the safety device itself is not shown. The syringe nose engagement face 30 and the cover end face 31 have relatively shallow conical profiles, with a conical angle of about 30°. This may give a tighter seal than that of the first embodiment, with a reduced compressive force.

FIGS. 8A, 8B, 9A and 9B show another embodiment where there is a generally rounded profile 33 at the nose of the syringe and a correspondingly rounded concave profile 34 within the cover end face. These matching profiles may provide a substantially airtight hermetic seal between the cover and the syringe. FIGS. 10A, 10B, 11A and 11B show yet another embodiment, this utilising a syringe nose defining a concave recess 36 having a central boss 37 within which the needle is carried and the cover has a profile at its rear end adapted to receive the central boss, the outer surface of the cover at its rear end being profiled to effect a seal to the recess 36.

With all of the above arrangements, the rearward portion 25 of the cover is subjected to a compressive force as the safety device is fitted on to the syringe by virtue of the interengagement of the step 27 with the internal forward end of the sleeve. As mentioned, other designs of safety device may be employed, with the cover being modified as appropriate to ensure that the rearward portion of the cover is subjected to a compressive force to maintain the rear end face thereof in sealing engagement with a corresponding engagement face of the syringe.

The invention claimed is:

1. A medical needle cover arrangement comprising:
    a syringe having a syringe barrel provided with a needle hub at a forward end thereof;
    a medical needle having a sharp tip mounted on the needle hub to project forwardly therefrom;
    a needle shield in the form of a sleeve having a diameter greater than a diameter of the syringe barrel, wherein the sleeve is slideably coupled to the syringe, and the needle shield is configured to transition between an initial shielding position and a non-shielding position, a forward end of the needle shield having an opening and a lip reducing an inside diameter of the needle shield; and
    a soft needle cover overlying the needle, the soft needle cover including:
        a forward portion extending beyond the needle shield and a rearward portion disposed within the needle shield such that the soft needle cover extends throughout the opening;
        a step engaging the lip; and
        a formation engaging the needle hub to effect a substantially airtight seal therebetween, wherein interengagement of the step with the lip and the formation with the needle hub subjects at least a portion of the soft needle cover to a compressive force along a longitudinal axis of the medical needle;
    wherein:
        the soft needle cover is resilient such that it is compressible radially to allow the step to pass through the opening and permit removal of the cover from the shield with the shield remaining coupled to the syringe.

2. A cover arrangement as claimed in claim 1, wherein the medical needle is secured in a bore of the needle hub.

3. A cover arrangement as claimed in claim 2, wherein there is an outwardly-directed formation extending at least partially around the needle hub of the syringe and a rear end of the soft needle cover is received on the needle hub, forwardly of the formation.

4. A cover arrangement as claimed in claim 1, wherein the sharp tip of the medical needle is received in a material of the soft needle cover so as to be sealed thereby.

5. A cover arrangement as claimed in claim 1, wherein the needle shield is a part of a needle safety device mounted on the syringe.

6. A cover arrangement as claimed in claim 5, wherein the needle safety device has a carrier attached to the forward end of the syringe, interengagement means being provided on the needle shield and on the carrier to block the needle shield against forward movement with respect to the syringe.

7. A cover arrangement as claimed in claim 1, wherein the formation on the needle hub comprises a nose at the forward end thereof having a nose engagement face at the forward end of the nose, and a corresponding formation at a rear end of the soft needle cover is a profile at the rear end of the soft needle cover.

8. A cover arrangement as claimed in claim 1, wherein the step is formed in an external surface of the soft needle cover.

9. A method of effecting a seal between a soft needle cover of a medical needle cover arrangement and a needle hub of a syringe, wherein a medical needle having a sharp tip projects forwardly from the needle hub and the syringe comprises a syringe barrel provided with the needle hub at a forward end thereof, the method comprising:

locating the soft needle cover within an opening at a forward end of a needle shield such that a forward portion of the soft needle cover extends beyond the needle shield and a rearward portion of the soft needle cover is disposed within the needle shield, the needle shield comprising a lip that reduces an inside diameter of the needle shield at the forward end of the needle shield; and slidably coupling the needle shield to the syringe in an initial shielding position such that the soft needle cover overlies the needle, wherein the needle shield is in the form of a sleeve that has a diameter greater than a diameter of the syringe barrel and the needle shield is configured to transition between the initial shielding position and a non-shielding position;

wherein:

the soft needle cover includes a step which engages with the lip of the needle shield and a formation engaging the needle hub, thereby forming a substantially airtight seal between an end face of the soft needle cover and the needle hub of the syringe by subjecting at least a portion of the soft needle cover to a compressive force along a longitudinal axis of the medical needle; and the soft needle cover is resilient such that it is compressible radially to allow the step to pass through the opening and permit removal of the cover from the shield with the shield remaining coupled to the syringe.

* * * * *